(12) United States Patent
Wagner et al.

(10) Patent No.: US 12,331,017 B2
(45) Date of Patent: Jun. 17, 2025

(54) PROCESS FOR STARTING UP AND SHUTTING DOWN A PLANT FOR REMOVING ISOBUTENE FROM A C4-HYDROCARBON MIXTURE

(71) Applicant: BASF SE, Ludwigshafen am Rhein (DE)

(72) Inventors: Hans-Guenter Wagner, Ludwigshafen am Rhein (DE); Suman Thotla, Ludwigshafen am Rhein (DE); Gerrit Waters, Ludwigshafen am Rhein (DE); Michael Huebner, Freeport, TX (US); Markus Neudert, Ludwigshafen am Rhein (DE); Randolph Hugo, Ludwigshafen am Rhein (DE); Thomas Roussiere, Ludwigshafen am Rhein (DE)

(73) Assignee: BASF SE, Ludwigshafen Am Rhein (DE)

( * ) Notice: Subject to any disclaimer, the term of this patent is extended or adjusted under 35 U.S.C. 154(b) by 112 days.

(21) Appl. No.: 18/280,688

(22) PCT Filed: Mar. 1, 2022

(86) PCT No.: PCT/EP2022/055185
§ 371 (c)(1),
(2) Date: Sep. 7, 2023

(87) PCT Pub. No.: WO2022/189217
PCT Pub. Date: Sep. 15, 2022

(65) Prior Publication Data
US 2024/0140887 A1    May 2, 2024

(30) Foreign Application Priority Data
Mar. 8, 2021   (EP) ..................... 21161187

(51) Int. Cl.
*C07C 7/04* (2006.01)
*B01D 3/14* (2006.01)
(Continued)

(52) U.S. Cl.
CPC .............. *C07C 7/04* (2013.01); *B01D 3/143* (2013.01); *C07C 1/24* (2013.01); *C07C 41/09* (2013.01)

(58) Field of Classification Search
CPC .. C07C 7/04; C07C 1/24; C07C 41/09; C07C 7/005; C07C 7/14891; C07C 41/42;
(Continued)

(56) References Cited

U.S. PATENT DOCUMENTS

| 4,287,379 A | 9/1981 | Brunner et al. |
| 2004/0097773 A1 | 5/2004 | Beckmann et al. |
| 2013/0245294 A1* | 9/2013 | Chewter ................... C07C 1/22 585/315 |

FOREIGN PATENT DOCUMENTS

EP    0003305 A2    8/1979

OTHER PUBLICATIONS

International Search Report and Written Opinion received for PCT Patent Application No. PCT/EP2022/055185, mailed on Jun. 7, 2022, 9 pages.

* cited by examiner

*Primary Examiner* — Ali Z Fadhel
(74) *Attorney, Agent, or Firm* — Faegre Drinker Biddle & Reath LLP

(57) ABSTRACT

The invention relates to a process for starting up a plant for removing isobutene from an isobutene-containing C4-hydrocarbon mixture, the plant comprising an etherification unit containing moist acidic ion exchange resin, a first distillation unit, an ether cleavage unit, and a second distil-
(Continued)

lation unit. The invention further relates to a process for shutting down the plant from a stationary operation mode.

13 Claims, 1 Drawing Sheet

(51) Int. Cl.
*C07C 1/24* (2006.01)
*C07C 41/09* (2006.01)

(58) Field of Classification Search
CPC ......... C07C 41/06; C07C 11/09; C07C 43/04; B01D 3/143
See application file for complete search history.

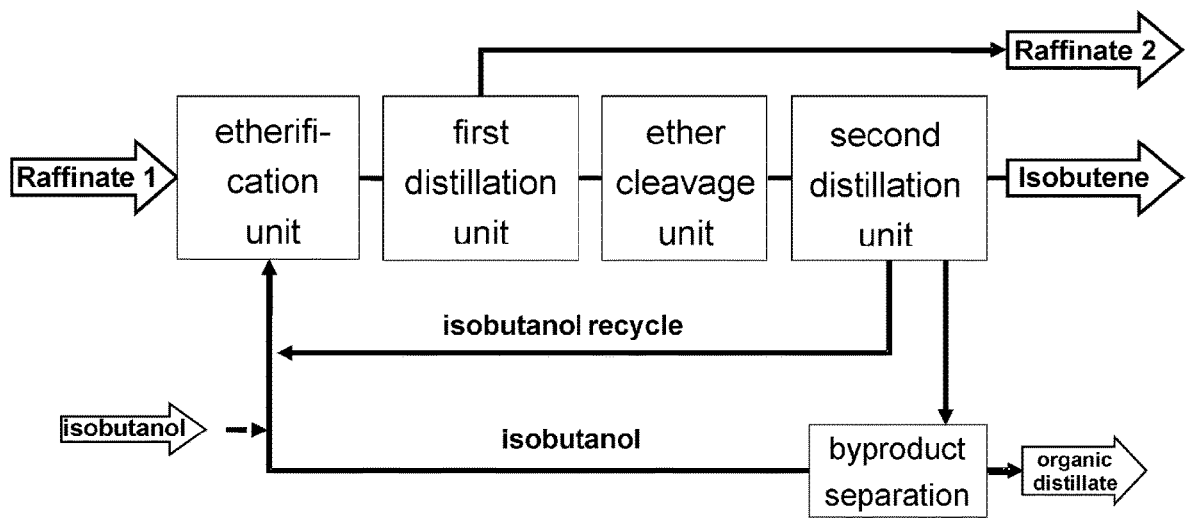

PROCESS FOR STARTING UP AND SHUTTING DOWN A PLANT FOR REMOVING ISOBUTENE FROM A C4-HYDROCARBON MIXTURE

CROSS-REFERENCE TO RELATED APPLICATIONS

This application is a National stage application (under 35 U.S.C. § 371) of PCT/EP2022/055185, filed Mar. 1, 2022, which claims benefit of European Application No. 21161187.6, filed Mar. 8, 2021, both of which are incorporated herein by reference in their entirety.

The present invention relates to processes for starting up and shutting down a plant for removing isobutene from a C4-hydrocarbon mixture.

C4 fractions from steam crackers or FCC units consist essentially of butadiene, isobutene, 1-butene and 2-butenes together with the saturated hydrocarbons isobutane and n-butane. Customary work-up methods used worldwide for such C4 fractions include the following steps: first, the major part of the butadiene is removed. A hydrocarbon mixture referred to as Raffinate 1, that includes the saturated hydrocarbons together with isobutene, 1-butene and 2-butenes remains. A possible way of removing the isobutene from this mixture is reaction with a primary alcohol to form an alkyl tert-butyl ether. This leaves the saturated hydrocarbons and linear butenes. The C4 mixture obtained after removal of the butadiene and isobutene is referred to as Raffinate 2.

EP 0003305 A2 discloses a process for removing isobutene from a isobutene-containing C4-hydrocarbon mixture, which comprises (a) reacting the mixture with a primary alcohol in the presence of an acidic ion exchange resin to form an alkyl tert-butyl ether; (b) distilling the reaction mixture to obtain a top product comprising the unconverted hydrocarbons, and a bottom product comprising the alkyl tert-butyl ether; (c) feeding the bottom product to a ether cleavage unit to decompose the alkyl tert-butyl ether to obtain isobutene and primary alcohol; (d) distilling the mixture of isobutene and primary alcohol produced in step (c) to obtain a top product comprising isobutene, and a bottom product comprising the primary alcohol; and (e) recycling the bottom product of step (d) to step (a).

Acidic ion exchangers are commercially available in a moist, hydrated state, i.e., they are swelled in water and covered by water. Also, the loading of the etherification unit with the acidic ion exchange resin usually involves filling the unit with water prior to loading the resin to ensure proper settling of the resin and avoid damage of the resin. Then, the packed bed is usually back-washed with water to remove fines. However, the presence of water in the process leads to unwanted side reactions. Most notably, the water reacts with isobutene to yield isobutanol, causing a considerable loss of isobutene.

Since water is not readily soluble in C4-hydrocarbons such as Raffinate 1, the moisture originating from the moist hydrated ion exchanger cannot sufficiently be removed from the etherification zone by purging with Raffinate 1 or other hydrocarbon mixtures.

Hence, there is a need for a starting up-procedure that efficiently removes the water entrained by the acidic ion exchange resin within a short time.

The need is met by a process for starting up a plant for removing isobutene from an isobutene-containing C4-hydrocarbon mixture, the plant comprising an etherification unit containing moist acidic ion exchange resin, a first distillation unit, an ether cleavage unit and a second distillation unit, the process comprising
  (a) filling the etherification unit with isobutanol;
  (b) filling the first distillation unit with C4-hydrocarbon and/or isobutanol, and operating the first distillation unit with total reflux;
  (c) filling the second distillation unit with C4-hydrocarbon and/or isobutanol, and operating the second distillation unit with total reflux;
  (d) withdrawing a bottom product of the second distillation unit, removing water from the bottom product and directing the bottom product to the etherification unit;
  (e) directing a discharge of the etherification unit to the first distillation unit;
  (f) directing a bottom product of the first distillation unit to the second distillation unit while bypassing the ether cleavage unit;
  (g) after the bottom product of the second distillation unit is essentially free of water, providing a flow of isobutene-containing C4-hydrocarbon mixture into the etherification unit and reacting the mixture with isobutanol to form a mixture of isobutyl tert-butylether (IBTBE) and unconverted hydrocarbons;
  (h) directing the mixture of IBTBE, unconverted hydrocarbons and unreacted isobutanol from the etherification unit to the first distillation unit and distilling the mixture to obtain a top product comprising the unconverted hydrocarbons, and a bottom product comprising IBTBE and unreacted isobutanol;
  (i) after IBTBE in the bottom product of the first distillation unit has reached a predetermined concentration, directing the bottom product of the first distillation unit to the ether cleavage unit to decompose the IBTBE to obtain isobutene and isobutanol;
  (j) directing the mixture of isobutene and isobutanol produced in step (i) to the second distillation unit and distilling the mixture of isobutene and isobutanol to obtain a top product comprising isobutene, and a bottom product comprising isobutanol; and
  (k) recycling the bottom product obtained in step (j) at least partially to the etherification unit.

The invention also relates to a process for shutting down a plant for removing isobutene from an isobutene-containing C4-hydrocarbon mixture, wherein stationary operation of the plant comprises (a) reacting an isobutene-containing C4-hydrocarbon mixture with isobutanol in the presence of an acidic ion exchange resin in an etherification unit to form a mixture of IBTBE and unconverted hydrocarbons; (b) distilling the reaction mixture in a first distillation unit to obtain a top product comprising the unconverted hydrocarbons, and a bottom product comprising IBTBE; (c) feeding the bottom product to a ether cleavage unit to decompose the IBTBE to obtain isobutene and isobutanol; (d) distilling the mixture of isobutene and isobutanol produced in step (c) in a second distillation unit to obtain a top product comprising isobutene, and a bottom product comprising isobutanol; and (e) recycling the bottom product of step (d) to step (a);
  the shutting down process comprising
  aa) taking the ether cleavage unit out of service and purging the ether cleavage unit with an inert gas; while the etherification unit, the first distillation unit and the second distillation unit stay in operation;
  bb) stopping the flow of isobutene-containing C4-hydrocarbon mixture into the etherification unit;
  cc) taking the etherification unit out of service;
  dd) operating the first distillation unit and the second distillation unit in total reflux mode; and ee) stopping the first distillation unit and the second distillation unit.

Start Up

For startup, the etherification zone is filled with isobutanol. Water is fairly soluble in isobutanol. Hence, any water contained in the bed of acidic ion exchange resin will be taken up by the isobutanol.

The first distillation unit and the second distillation unit will be taken into service by filling with at least one of C4-hydrocarbons and isobutanol. For start up, the columns are operated in total reflux. "Total reflux" means that no overhead product distillate is being withdrawn from the column and the vapor withdrawn at the top is fully condensed and returned to the column. Any C4-hydrocarbon or C4-hydrocarbon mixture can be used to this end depending on availability. However, in order to shorten the time necessary to establish equilibrium in the distillation column and obtain specification-compliant product at the top it may be convenient to fill the first distillation unit and/or the second distillation unit with a C4-hydrocarbon having a composition close to or conforming to the specification of the top product withdrawn during productive operation. Hence, in an embodiment, the first distillation unit is filled with C4-hydrocarbons other than isobutene, in particular Raffinate 2. Startup can be accelerated when high purity isobutene is available for filling the second distillation unit. Hence, in an embodiment, in step (c), the second distillation unit is filled with isobutene.

Then the recycle isobutanol loop is taken into service while the ether back-splitting unit is bypassed. By taking up Raffinate 1 the etherification reaction sets in and IBTBE will be produced.

Preferably in step (d), water is removed from the bottom product by distillation.

The top product of the first distillation unit is discarded and as soon as the recycle isobutanol stream is free of water and the concentration of IBTBE bottom product of the first distillation unit has reached a predetermined concentration, the ether back-splitting unit will be taken into service. Preferably, the minimum predetermined IBTBE concentration is 50%, more preferably 70% to 80%.

Step (i) involves switching from bypassing the ether cleavage unit to stationary operation of the ether cleavage unit. The switching suitably occurs in a staggered manner. When starting up, the evaporator (such as a Robert evaporator) is first run with a small amount of feed (i.e., bottom product of the first distillation unit) until any inert gas (nitrogen) in the cleavage reactor(s) is displaced by evaporation of the feed whereas the remainder is passed past the ether cleavage unit. During this period, the output from the ether cleavage unit is discarded, e.g., vented to a flare or into the exhaust system. Then, the cleavage reactor(s) are switched on while the connection to the downstream column is still closed and the outlet continues to be discarded. Then the feed to the evaporator and ether cleavage is increased until the cleavage product, i.e. the mixture of isobutene and isobutanol, at the outlet of the ether cleavage unit has reached the pressure of the downstream column, i.e. the second distillation unit. Then, the feed stream is completely switched from bypass to the ether cleavage unit.

Isobutene-containing C4-hydrocarbon mixture

Isobutene-containing C4-hydrocarbon mixtures suitable for the process of the invention are obtained, for example, from the thermal or catalytic cracking of petroleum products, from the pyrolysis of liquefied petroleum gas (LPG), naphtha, gas oil or the like, or from the catalytic dehydrogenation of n-butane and/or n-butene. In general, these C4-hydrocarbon mixtures contain olefinic and paraffinic C4-hydrocarbons in addition to the isobutene. They may also contain butadiene and acetylenes, e.g., but-1-yne and butenyne. Butadiene-containing C4-hydrocarbon mixtures may be employed as such or after removal of the butadiene from the C4-hydrocarbon mixture, for example by extraction with a selective solvent. In general, the isobutene-containing C4-hydrocarbon mixture contains from 5 to 95% by weight, preferably from 10 to 90% by weight, in particular from 20 to 70% by weight, of isobutene. Preferably, C4-hydrocarbon mixtures are used which in addition to isobutene contain n-butane, isobutane, but-1-ene, trans-but-2-ene and cis-but-2-ene, with or without buta-1,3-diene.

A hydrocarbon mixture referred to as Raffinate 1 is typically used for the process of the invention.

Etherification Unit

The etherification is based on the selective reaction of isobutanol with isobutene contained in the isobutene-containing C4-hydrocarbon mixture, such as Raffinate 1. The product formed is isobutyl-tert-butyl ether (herein referred to as "IBTBE"). Other C4-hydrocarbons do not participate in the etherification reaction. The etherification may be carried out in, for example, one or more stirred kettles or one or more fixed bed reactors, the latter being preferred.

The etherification reaction occurs in the presence of an acidic ion-exchange resin, which acts as a heterogeneous etherification catalyst. The acidic ion-exchange resin is a cation exchanger in the acid form. In one embodiment, the acidic ion-exchange resin comprises a sulfonic or phosphoric ion-exchange resin. Preferably, the acidic, ion-exchange resin comprises a macro-reticular ion-exchange resin. Examples of suitable ion exchange resins are sulfonated phenol-formaldehyde resins, sulfonated resins derived from coumarone-indene condensation products and, in particular, sulfonated polystyrene resins. In a preferred embodiment, the acidic ion-exchange resin comprises a copolymer of styrene and divinylbenzene, e.g., a cross-linked styrene-divinylbenzene copolymer, functionalized with sulfonic acid groups.

In an embodiment, the acidic, ion-exchange resin can have a concentration of acidic ion-exchange groups of at least about 1 milliequivalent $H^+$ per gram dry resin. In general, the amount of the ion exchange resin is from 0.01 to 1 liter of bulk volume per liter of reactor volume.

Preferably, the etherification is carried out continuously, in which case the quotient of the volume of the reaction zone (in volume units) and the throughput in volume units per hour is in general from 0.01 to 5 hours, preferably from 0.02 to 1 hour, especially from 0.03 to 1 hour.

In general, the etherification reaction results in not less than 90%, preferably not less than 95%, in particular not less than 96%, conversion of the isobutene, contained in the C4-hydrocarbon mixture, to IBTBE.

A molar excess of isobutanol in respect to isobutene is advantageous to reach a high conversion of isobutene and to suppress the formation of isobutene oligomers. The conversion increases with increasing molar ratio of isobutanol to isobutene. Once a steady state has been reached, the weight ratio of isobutanol to the isobutene contained in the C4-hydrocarbon mixture is in general from 100:1 to 1:1, preferably from 20:1 to 1.2:1, especially from 4:1 to 1.3:1.

The etherification can be carried out under atmospheric pressure. However, it is advantageous to work under super-atmospheric pressure, for example at from 1.01 to bar, especially from 2 to 20 bar. The isobutene-containing C4-hydrocarbon mixture can, depending on the pressure and temperature, be employed as a liquid or a gas. Preferably, liquid isobutene-containing C4-hydrocarbon mixtures are employed. The pressure will be kept in the range of 12 to 20 bar to ensure that no vaporization occurs within the etherification unit.

Preferably, the exit temperature of the reaction mixture from the etherification unit is from 25 to 65° C., preferably from 30 to 60° C., especially from 30 to 50° C. The etherification is an exothermic reaction. The etherification reaction is an equilibrium reaction and the ether formation is favored at low temperatures. In order to reach high reaction rates and high isobutene conversion along with low byproduct formation, the reactor system is preferably cascaded and temperatures below 70° C. are applied. In an embodiment, a plurality of adiabatic fixed bed reactors are used in series, e.g., three adiabatic fixed bed reactors. The typical reactor inlet temperature is in the range of 30 to 40° C. The conversion is highest in the first reactor, the second reactor converts the remaining isobutene and the last reactor has a larger residence time to achieve the equilibrium condition of the etherification reaction.

With increasing age of the catalyst, the main contribution to the total conversion shifts from first to second reactor. The inlet temperature of the reactors is adjusted to achieve the intended conversion and depends on the activity of each of the catalysts. The inlet temperature of the 3rd reactor will normally be the lowest and is kept as low as possible while still achieving equilibrium conditions at the outlet of this reactor.

In general, the catalyst of 1st reactor will be replaced more frequently than catalyst of 2nd and 3rd reactor as contaminants within the feedstock will deactivate catalyst of 1st reactor with a higher probability and conversion is typically highest within 1st reactor.

The recycle isobutanol contains a certain amount of IBTBE. The lower the content of IBTBE, the lower the molar excess of isobutanol can be chosen and/or the conversion can be increased.

First Distillation Unit

The reaction mixture withdrawn from the etherification unit contains IBTBE, unconverted hydrocarbons and unreacted isobutanol. The C4-hydrocarbons, which have not participated in the etherification reaction are separated from the IBTBE and the excess isobutanol in a first distillation unit. The top product taken off is a C4-hydrocarbon raffinate substantially free from isobutene. In general, the isobutene content is 5% by weight or less, preferably 2.5% by weight or less, especially 1.5% by weight or less. The isobutene content within the top product is determined by the conversion in the etherification unit and the initial composition of the isobutene-containing C4-hydrocarbon mixture, e.g., Raffinate 1. The isobutene content within the top product can be reduced by recycling part of the top product to the etherification unit.

Preferably, the combined amount of IBTBE and/or di-isobutyl ether in the top product is not more than 200 ppm by weight. The top product is called Raffinate 2.

The bottom product from the first distillation unit consists of IBTBE which may or may not still contain excess isobutanol. Advantageously, a bottom product containing not more than 1,000 ppm by weight, preferably not more than 500 ppm by weight, especially not more than 100 ppm by weight, of C4-hydrocarbons is taken off.

Conveniently, the first distillation unit is operated under a pressure of about 4 to 8 bar and the bottom temperature is 165 to 175° C., for example about 170° C. Non-condensables, e.g., nitrogen and C3 hydrocarbons are discharged as off-gas.

As Raffinate 1 can contain dissolved water, water is removed from the reflux drum of the tower.

The bottom product of the first distillation unit contains IBTBE, non-reacted isobutanol and other higher boiling compounds. After a steady state has been reached, the bottom product is transferred, e.g. by a pump, to the ether cleavage unit.

Ether Cleavage Unit

In the ether cleavage unit, the IBTBE is decomposed into isobutene and isobutanol in the presence of an acid catalyst at elevated temperatures. Preferably, the IBTBE-containing bottom product from the first distillation unit is transferred to the ether cleavage unit without removal of any excess isobutanol which may be present. Alternatively, it is possible to remove part or all of the isobutanol.

The IBTBE-containing bottom product from the first distillation unit is vaporized, superheated (to prevent condensation on the ether cleavage catalyst due to endothermic reaction and pore condensation) and brought into contact with the acid catalyst in the vapor phase. Possible vaporizers are all customary types of vaporizer, e.g. falling film evaporators, helical tubes, thin film evaporators, natural convection evaporators with external or internal circulation, for example a Robert evaporator, or forced circulation evaporators. Preference is given to a Robert evaporator or a falling film evaporator.

The decomposition of the tertiary ether may be carried out batchwise but is preferably carried out continuously.

The ether-cleavage reaction is an equilibrium reaction and the splitting is favored by high temperatures. The typical conversion is greater than 90%. Useful reactors include heated tubular reactors, such as steam-heated tubular reactors, or two reactor systems consisting of a heated tubular reactor followed by an adiabatic fixed bed reactor.

Examples of suitable acid catalysts are ion exchangers in the acid form, e.g., sulfonated coal, sulfonated phenol-formaldehyde resins, sulfonated resins derived from coumarone-indene condensation products and, in particular, sulfonated polystyrene resins, e.g., sulfonated, crosslinked styrene-divinylbenzene copolymers.

Other catalysts which may be used advantageously are solid phosphoric acid catalysts which comprise monophosphoric acid or preferably polyphosphoric acid on a solid carrier. Examples of suitable carriers for the phosphoric acid catalysts are alumina, silica, active charcoal, kieselguhr or pumice. Silica gel is the preferred carrier.

Other suitable acid catalysts are metal sulfates, e.g., sodium bisulfate, calcium bisulfate, aluminum sulfates, nickel sulfate, copper sulfate, cobalt sulfate, cadmium sulfate and strontium sulfate. These sulfates may be used unsupported but are preferably used on a carrier. Examples of suitable carriers are silica gel, active charcoal, alumina and pumice.

Further suitable catalysts for the decomposition are silica gel or alumina as such.

In a further embodiment of the process according to the invention, a metal phosphate, especially a metal hydrogen phosphate, is used as the acid decomposition catalyst. These phosphates may also contain phosphoric acid in excess over the amount corresponding to the stoichiometric composition of the acid metal phosphate, for example in an excess of up to 65%, preferably from 1 to 50%, in particular from 10 to 20%. Examples of such metal phosphates are magnesium phosphates, calcium phosphates, strontium phosphates, barium phosphates, manganese phosphates, nickel phosphates, copper phosphates, cobalt phosphates, cadmium phosphates, iron (II) phosphates, chromium phosphates and in particular aluminum phosphates. The metal phosphate catalyst can be used as such or on a carrier. Examples of suitable carriers are alumina, silica, active charcoal and zinc oxide.

The amount of the acid catalyst is in general from about 0.01 to 1 kg, preferably from about 0.03 to 0.3 kg, per kg of IBTBE passed through the reactor per hour. Preferably, fixed bed reactors are used for the decomposition of the IBTBE.

The decomposition temperature of the tertiary ether varies with the nature of the acid catalyst and with the contact time, but is in general from 50° C. to 350° C., preferably from 80° C. to 300° C., in particular from 100° C. to 250° C. If a metal phosphate or phosphoric acid catalyst is used as the decomposition catalyst, the decomposition is in general carried out at from 80° C. to 350° C., preferably from 90° C. to 260° C., especially from 170° C. to 210° C.

The contact time of the vaporized tertiary ether is advantageously from 0.1 to 20 seconds, preferably from 1 to 10 seconds.

The decomposition of the tertiary ether can be carried out under atmospheric pressure, but is in general carried out under superatmospheric pressure, for example at up to 30 bar, preferably up to 20 bar. Advantageously, the decomposition of the tertiary ether is carried out under pressures of from 2 to 15 bar, preferably from 3 to 12 bar, especially from 4 to 12 bar. However, the decomposition can also be carried out under reduced pressure.

In an embodiment, the ether cleavage unit comprises a first ether cleavage reactor and a second ether cleavage reactor connected in series. In step (i) the second ether cleavage reactor is bypassed until activity of first ether cleavage reactor lowers. Due to high initial activity of first ether cleavage reactor nearly full conversion is reached in this reactor. The absence of cleavable ether in the output of the first reactor may give rise to undesired side reactions in the second reactor, such as dehydratization of isobutanol to $H_2O$ and isobutene. When the activity of first ether cleavage reactor lowers over time and the output of the first ether cleavage reactor contains a predetermined concentration of IBTBE, the second ether cleavage reactor is taken into operation.

In preferred embodiments, the first ether cleavage reactor and the second ether cleavage reactor are periodically caused to alternate in sequence and/or flow direction through the first ether cleavage reactor and/or the second ether cleavage reactor is periodically changed. The possibility to switch between the two reactors and to periodically change flow direction through reactors may lead to more uniform deactivation over the reactor length and better reaction control. Ultimately, overall runtime can be improved.

Second Distillation Unit

The reaction mixture obtained from the ether-cleavage unit, which contains isobutene and isobutanol as the reaction products, is fed to a second distillation unit. In the second distillation unit, high purity isobutene is separated from heavier compounds such as isobutanol, non-reacted IBTBE, and further heavier compounds, e.g. di-isobuten (DIB), by distillation. The second distillation unit is operated under a pressure of about 4-8 bar and the bottom temperature is about 160° C. (5 bar).

Advantageously, the top product contains not less than 99.3% by weight, preferably not less than 99.5% by weight, especially not less than 99.7% by weight, of isobutene. Preferably, isobutene containing not more than 500, preferably not more than 100, especially not more than 50, ppm by weight of isobutanol is taken off as the top product.

Preferably, the high purity isobutene product is taken off from a side draw of the second distillation unit close to the top. Any water which is created by back-splitting isobutanol is removed from the system by the reflux drum.

The bottom product consists mainly of isobutanol and IBTBE. The major part of the bottom product is supplemented with fresh isobutanol from isobutanol feed drum and then sent back to the etherification unit.

Isobutanol Bleed Stream and Byproduct Separation Unit

Advantageously, a small portion of the bottom product from the second distillation unit is taken off as a bleed stream in order to remove the undesired heavies, such as diisobutyl ether, from the system. This stream is sent to a byproduct separation unit. Hence, preferably part of the bottom product obtained in step (j) is directed to a byproduct separation unit where high boiling byproducts are separated from the isobutanol. The weight ratio of bottom product directed to the byproduct separation unit to bottom product recycled to the etherification unit may in the range of from 1:20 to 2:10, preferably about 1:10.

The most important side reaction is the formation of di-isobutene (DIB) and tri-isobutenes (TIB). Other possible reactions are negligible. Over time even these components can accumulate in the system and have to be removed in the byproduct separation unit.

The bleed stream taken off from the bottom of the second distillation unit is forwarded to a byproduct separation unit. The byproduct separation is required to prevent the accumulation of undesired side components within the recycle isobutanol stream. Depending on the economic feasibility a minimum of 2 distillation towers is recommended. A three-tower system should be considered for achieving a high recovery rate of isobutanol. The recovered isobutanol is returned to the isobutanol feed drum. The remaining hydrocarbons are discarded.

In an embodiment of the process, the isobutanol bleed-stream is dehydrated in the presence of a dehydrating catalyst, resulting in the dehydration of not only the isobutanol but also the diisobutyl ether, and thereby additionally increasing the yield of isobutene. Advantageously, the dehydration is carried out in the gas phase over a catalyst. Examples of suitable catalysts are silica gel, thorium oxide, titanium (IV) oxide and especially alumina. In general, the dehydration is carried out at from 250° C. to 450° C., preferably from 300° C. to 400° C. It can be advantageous to carry out the dehydration in the presence of water, which may or may not be added for the purpose.

Shutdown

The byproduct separation unit can be stopped for a certain time without significant effect on the process. Since the formation of high boiling byproducts, e.g. diisobutanol or triisobutanol, occurs with a low rate, accumulation of these high boiling byproducts to unacceptable levels takes some time.

A controlled shutdown of the plant can be executed in a staged manner. At first the ether cleavage unit will be taken out of service and purged with nitrogen while the remaining units of the plant stay in operation. "Taking out of service" means bypassing the ether cleavage and turning off the conditions conducive to ether cleavage, in particular cooling the reactors below reaction temperature. As no more isobutene and isobutanol are formed in the ether cleavage unit, no more isobutanol is recycled to the etherification unit. The molar ratio of isobutanol over isobutene in the etherification unit decreases. As soon as the ratio decreases below a predetermined value, the flow of isobutene-containing C4-hydrocarbon mixture into the etherification unit will be stopped.

As a next step, the etherification unit will be taken out of service. The first distillation unit, second distillation unit and byproduct separation can be operated in total reflux mode. As a final step the distillations will be stopped.

Island Mode:

The stationary operation of the above-described plant for removing isobutene from an isobutene-containing C4-hydrocarbon mixture relies on a continuous source of process inputs, notably the isobutene-containing C4-hydrocarbon mixture such as Raffinate 1 feedstock. In case that there is a temporary shortage or unavailability of isobutene-containing C4-hydrocarbon mixture, the plant can be brought into "Island Mode". To this end, the product streams will be directed to the inlet of the plant. Specifically, the top product comprising the unconverted hydrocarbons obtained in the first distillation unit, and the top product comprising isobutene obtained in the second distillation unit are directed to the etherification unit. Hence, the plant will continue operating normally, however being independent from feedstock and product pipelines. This allows for a smooth transition as soon as the process inputs and product pipelines are available again at the expense of an ongoing energy demand.

While after a shutdown of the ether cleavage unit or the whole plant, it will take some time to start up the production again, the transition from Island Mode to stationary operation is seamless.

The invention is illustrated by the FIGURE which is appended.

BRIEF DESCRIPTION OF FIGURE

FIG. 1 is a block flow diagram of the plant for removing isobutene from a C4-hydrocarbon mixture.

As shown in FIG. 1, isobutene-containing C4-hydrocarbon mixture is passed to the etherification unit which contains the ion exchanger, to which also a stream of isobutene is directed. Advantageously, the unit comprises a fixed bed reactor, e.g., a flow tube or a loop reactor or a combination of both types. The reaction mixture obtained is to a first distillation unit. At the top of the first distillation unit, substantially isobutene-free C4-hydrocarbon raffinate is taken off. IBTBE which is obtained as the bottom product of the first distillation unit and which may contain excess isobutanol is fed to the ether cleavage unit where it is vaporized and, after vaporization, is passed into a reactor containing acid catalyst. This reactor is in general a fixed bed reactor. The mixture of isobutene and isobutanol taken from the ether cleavage unit is passed into the second distillation unit where pure isobutene is obtained as the top product. Isobutanol obtained as the bottom product is returned to the etherification unit, where necessary after replenishing isobutanol. Advantageously, a bleed-stream is taken off to remove any impurities formed, e.g., diisobutyl ether, diisobutene or triisobutene.

The invention claimed is:

1. A process for starting up a plant for removing isobutene from an isobutene-containing C4-hydrocarbon mixture, the plant comprising an etherification unit containing moist acidic ion exchange resin, a first distillation unit, an ether cleavage unit, and a second distillation unit, the process comprising
(a) filling the etherification unit with isobutanol;
(b) filling the first distillation unit with C4-hydrocarbon and/or isobutanol, and operating the first distillation unit with total reflux;
(c) filling the second distillation unit with C4-hydrocarbon and/or isobutanol, and operating the second distillation unit with total reflux;
(d) withdrawing a bottom product of the second distillation unit, removing water from the bottom product and directing the bottom product to the etherification unit;
(e) directing a discharge of the etherification unit to the first distillation unit;
(f) directing a bottom product of the first distillation unit to the second distillation unit while bypassing the ether cleavage unit;
(g) after the bottom product of the second distillation unit is essentially free of water, providing a flow of isobutene-containing C4-hydrocarbon mixture into the etherification unit and reacting the isobutene-containing C4-hydrocarbon mixture with isobutanol to form a mixture of IBTBE and unconverted hydrocarbons;
(h) directing the mixture of IBTBE, unconverted hydrocarbons and unreacted isobutanol from the etherification unit to the first distillation unit and distilling the mixture to obtain a top product comprising the unconverted hydrocarbons, and a bottom product comprising IBTBE and unreacted isobutanol;
(i) after IBTBE in the bottom product of the first distillation unit has reached a predetermined concentration, directing the bottom product of the first distillation unit to the ether cleavage unit to decompose the IBTBE to obtain isobutene and isobutanol;
(j) directing the mixture of isobutene and isobutanol produced in step (i) to the second distillation unit and distilling the mixture of isobutene and isobutanol to obtain a top product comprising isobutene, and a bottom product comprising isobutanol and;
(k) recycling the bottom product obtained in step (j) at least partially to the etherification unit.

2. The process according to claim 1, wherein in step (b), the first distillation unit is filled with C4-hydrocarbons other than isobutene.

3. The process according to claim 1, wherein in step (c), the second distillation unit is filled with isobutene.

4. The process according to claim 1, wherein in step (i), the predetermined IBTBE concentration is 50%.

5. The process according to claim 1, wherein in step (d), water is removed from the bottom product by distillation.

6. The process according to claim 1, wherein a part of the top product obtained in step (h) is recycled to the etherification unit.

7. The process according to claim 1, wherein the etherification unit comprises a plurality of fixed bed reactors in series.

8. The process according to claim 1, wherein the ether cleavage unit comprises a first ether cleavage reactor and a second ether cleavage reactor connected in series, and in step (i) the second ether cleavage reactor is bypassed until activity of first ether cleavage reactor lowers.

9. The process according to claim 8, wherein the first ether cleavage reactor and the second ether cleavage reactor are periodically caused to alternate in sequence and/or flow direction through the first ether cleavage reactor and/or the second ether cleavage reactor is periodically changed.

10. The process according to claim 1, comprising directing part of the bottom product obtained in step (j) to a byproduct separation unit and separating high boiling byproducts from the isobutanol.

11. The process of claim 10, wherein the weight ratio of bottom product directed to the byproduct separation unit to bottom product recycled to the etherification unit is in the range of from 1:20 to 2:10.

12. The process according to claim 1, wherein the acidic ion exchange resin is a cross-linked styrene-divinylbenzene copolymer functionalized with sulfonic acid groups.

13. A process for shutting down a plant for removing isobutene from an isobutene-containing C4-hydrocarbon mixture, wherein stationary operation of the plant comprises
(a) reacting an isobutene-containing C4-hydrocarbon mixture with isobutanol in the presence of an acidic ion exchange resin in an etherification unit to form a mixture of IBTBE and unconverted hydrocarbons;
(b) distilling the reaction mixture in a first distillation unit to obtain a top product comprising the unconverted hydrocarbons, and a bottom product comprising IBTBE;
(c) feeding the bottom product to a ether cleavage unit to decompose the IBTBE to obtain isobutene and isobutanol;
(d) distilling the mixture of isobutene and isobutanol produced in step (c) in a second distillation unit to obtain a top product comprising isobutene, and a bottom product comprising isobutanol; and
(e) recycling the bottom product of step (d) to step (a);
the shutting down process comprising
aa) taking the ether cleavage unit out of service and purging the ether cleavage unit with an inert gas; while the etherification unit, the first distillation unit and the second distillation unit stay in operation;
bb) stopping the flow of isobutene-containing C4-hydrocarbon mixture into the etherification unit;
cc) taking the etherification unit out of service;
dd) operating the first distillation unit and the second distillation unit in total reflux mode; and
ee) stopping the first distillation unit and the second distillation unit.

\* \* \* \* \*